United States Patent [19]

McRae

[11] Patent Number: Plant 6,367

[45] Date of Patent: Nov. 1, 1988

[54] LILY PLANT NAMED 'LEMON PIXIE'

[75] Inventor: Edward A. McRae, Boring, Oreg.

[73] Assignee: Melridge, Inc., Aurora, Oreg.

[21] Appl. No.: 929,270

[22] Filed: Nov. 10, 1986

[51] Int. Cl.[4] ..... A01H 5/00

[52] U.S. Cl. ..... Plt./68

[58] Field of Search ..... Plt./68

*Primary Examiner*—James R. Feyrer

*Attorney, Agent, or Firm*—Charles W. Rummler

[57] ABSTRACT

A new variety of hybrid lily plant having an average height of less than eighteen inches and bearing large clusters of medium sized, upright flowers distinguished by their lemon yellow coloration which is accented by a "ring" of small, deep magenta spots surrounding the center of each flower, the flowers being of excellent form and long persistence. This plant has abundant foliage comprising moderately long and full leaves which, together with the short stature of the plant and its upright flowers, make it especially suitable as a pot plant variety. This plant is highly resistant to disease and shows high tolerance of virus, making it an excellent garden plant, and the bulbs of this plant when dug may be precooled and forced throughout the year for pot plant production, the clone being vigorous and a good grower and propagator.

1 Drawing Sheet

BACKGROUND OF THE INVENTION

This new variety of lily plant originated as a seedling selected from a group of seedlings resulting from a crossing made by me at Sandy, Oreg., in which I used a very short, unnamed and unpatented, cream-flowered clonal section from the 'Pastel Hybrids' strain as the seed parent and an unnamed and unpatented golden yellow-flowered seedling from 'Connecticut Lemonglow'×'Red Carpet' as the pollen parent, both unpatented. The object of these breeding efforts was the production of lilies in shades of yellow well suited to forcing for pot plant production out of season.

This particular seedling was selected for propagation because of the upright orientation of the vivid yellow coloration of its medium large to large size flowers and the selected plant was asexually reproduced by me at Sandy, Oreg., with such satisfactory results that propagation was continued under my direction through successive generations, by bulb scale propagation and by natural propagation from bulblets, and this extensive propagation demonstrated that the novel and distinctive characteristics of this new plant are fixed and would hold true, under asexual propagation, from generation to generation.

DESCRIPTION OF THE DRAWING

My new variety of lily plant is illustrated by the accompanying photographic drawing showing buds and fully opened flowers, the colors shown being as close as it is reasonably possible to obtain by conventional photographic procedures.

DESCRIPTION OF THE NEW VARIETY

The following is a detailed description of my new variety of Asiatic hybrid lily with nomenclature according to The International Lily Register of The Royal Horticultural Society of London, England (Second Edition, 1969), and with color designations according to the R.H.S. Colour Chart of The Royal Horticultural Society published in 1966.

THE PLANT

Origin: Seedling

Parentage:

*Seed parent.*—Very short, cream flowered clonal selection from the 'Pastel Hybrids' strain.

*Pollen parent.*—Golden yellow-flowered selection from 'Connecticut Lemonglow'×'Red Carpet', both unpatented.

Classification:

*Horticultural.*—Upright Asiatic Hybrid Lily, Division I-A of the Horticultural Classification of Lilies by The Royal Horticultural Society of London, England.

*Commercial.*—Hybrid Lily Cultivar.

Form: Single stem, erect and stately.

Height: About 30 to 40 cm., by glasshouse forcing of bulbs about 12 to 18 cm. in circumference, with adequate light levels.

Growth: Vigorous and upright.

Foliage:

*Quantity*—Abundant.

*Leaf size.*—About 8 to 12 cm. long and about 1 cm. wide, in average. p2 *Leaf shape.*—Lanceolate with acute tip.

*Texture.*—Leathery.

*Aspect.*—Glossy with light pubescent margins and at the leaf axils.

*Color.*—Dark green, somewhat lighter on the under side.

Bulbs:

*Size.*—Depending upon age, up to about 25 cm. in circumference in commercial use.

*Color.*—White.

THE BUD

Form: Long, ovoid and obtuse.

Size: About 8 to 9 cm. long and about 5 cm. in circumference just prior to opening. p0 Opening rate: The Opening rate: The bud opens slowly, in about one hour in response to morning light.

bud opens slowly, in about one hour in response to morning light.

Color: Soft yellow with green apex just prior to opening and as the tepals unfurl.

Peduncle:

*Length.*—Averages about 4 to 6 cm., but may lengthen if light levels are too low or if bulbs have been improperly stored prior to forcing.

*Color.*—Dark green with soft plum overlay.

THE FLOWER

Blooming habit: Once annually and profusely in midseason for Asiatic lilies.

Size: Medium, averaging about 12 to 15 cm. in diameter.

Borne: Racemose on a single stem with 5 to 8 buds from a bulb about 12 to 16 cm. in circumference.

Shape: Cup-shaped upon first opening then becoming flattened as the tepals recurve during the second day.

Tepalage:

*Number.*—Six.

*Arrangement.*—Hexagonal and imbricated.

*Shape.*—Ovate with entire margins and obtuse tip.

*Appearance.*—Shiny.

*Color.*—Lemon yellow, 9B-C, occasionally lightened by a soft green flush at the center of the flower when it first opens. The nectaries are green with white pubescence.

*Spotting.*—There is a ring about 3.5 cm. wide of small, deep magenta spots surrounding the center of each flower, the ring being formed of a group of small spots on each side of the nectary channel adjacent the base of each tepal.

*Color changes.*—The color deepens to 12A-B as the flower ages with adequate light levels for cut flower and pot plant maintenance.

Pedicel:

*Length.*—About 4 to 8 cm.

*Form.*—Sturdy and ascending up to about 60° from the horizontal; very rarely having secondary buds.

*Color.*—Dark green with soft plum overlay.

Persistence: The tepals stay on the stems for about 3 weeks.

Fragrance: None.

Disease resistance: The flower and plant are resistant to disease, particularly Botrytis blight and Fusarium bulb rot as observed in western Oregon.

Lasting quality: The flower is long lasting.

THE REPRODUCTIVE ORGANS

Stamens:

*Number.*—Six.

*Arrangement.*—Typical of the genus Lilium.

*Anthers and pollen.*—Color: Greyed orange, 167A.

*Filaments.*—Length: About 5 cm. Color: Soft cream, 12D.

Pistils:

*Number.*—One.

*Length.*—About 5 cm.

*Stigma.*—Of medium size and with deep magenta-plum color.

Ovary: Characteristic of genus Lilium.

THE FRUIT

Fertility: The fruit is fertile.

Shape: Ovoid.

Color at maturity: Soft brown, sometimes overlaid with soft plum.

This new lily variety closely resembles the variety 'Sunray' but it is distinguished by the flowers being upright and having a decorative ring of spots surrounding the flower center and the tepals having slightly fluted edges; a higher bud count, with a more compact inflorescence; and a shorter height with longer leaves. It is also more reliable and uniform then 'Sunray' in its forcing performance.

I claim:

1. A new and distinct variety of Asiatic hybrid lily, substantially as herein shown and described, particularly distinguished by the unique color pattern of its flowers which are characterized by a ring of deep magenta spots surrounding the center of the flower, and the excellence of its flower form; the plant has a vigorous growth habit with rapid natural propagation; and its short stemmed, abundantly leaved and upright flowering silhouette as a pot plant specimen.

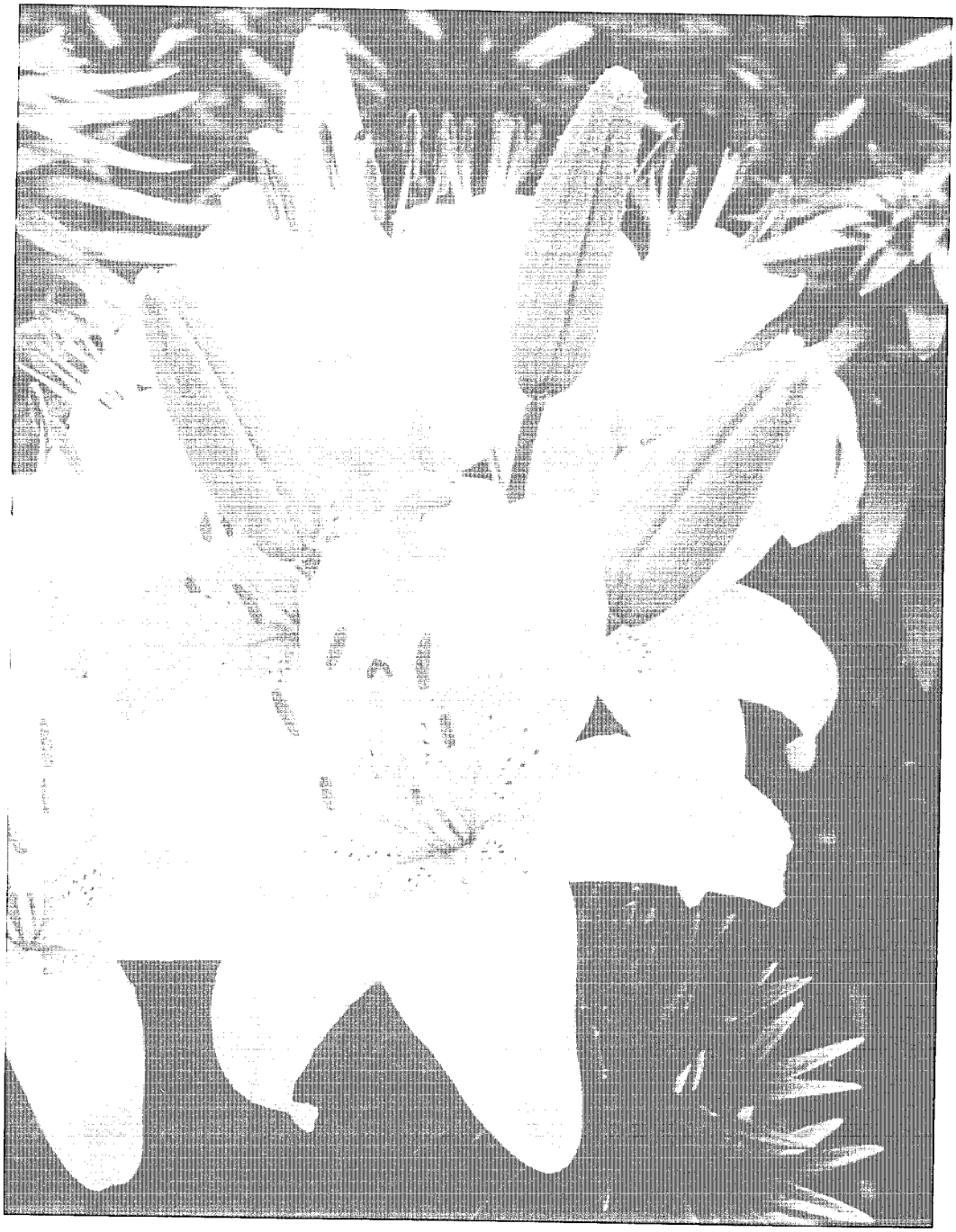

* * * * *